United States Patent [19]

Petzoldt

[11] Patent Number: 4,696,948
[45] Date of Patent: Sep. 29, 1987

[54] INDANYL DERIVATIVES AND PROCESS FOR THEIR PREPARATION

[75] Inventor: Karl Petzoldt, Berlin, Fed. Rep. of Germany

[73] Assignee: Schering Aktiengesellschaft, Berlin and Bergkamen, Fed. Rep. of Germany

[21] Appl. No.: 675,596

[22] Filed: Nov. 28, 1984

[30] Foreign Application Priority Data

Nov. 28, 1983 [DE] Fed. Rep. of Germany ....... 3343331

[51] Int. Cl.⁴ .................... A01N 41/06; A61K 31/18; C07C 143/74
[52] U.S. Cl. ........................ 514/605; 564/99
[58] Field of Search .................... 564/99; 514/605

[56] References Cited

U.S. PATENT DOCUMENTS 4,244,960  1/1981  Schroder et al. ............... 424/263
4,375,479  3/1983  Schroeder et al. ............. 424/321

OTHER PUBLICATIONS

Krause et al., *Xenobiotica* 1983, vol. 13, No. 5, pp. 265–272.

*Primary Examiner*—Paul F. Shaver
*Attorney, Agent, or Firm*—Millen & White

[57] ABSTRACT

Indanyl compounds of the formula

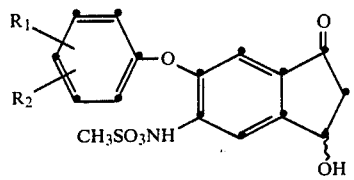

wherein $R_1$ and $R_2$ are hydrogen, fluorine or chlorine, is useful in the treatment of inflammatory and allergic diseases are prepared by fermenting indanyl compounds of the formula

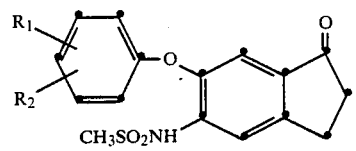

with a culture of *Aspergillus niger* or *Polyporus tulipiferus*.

6 Claims, No Drawings

INDANYL DERIVATIVES AND PROCESS FOR THEIR PREPARATION

BACKGROUND OF THE INVENTION

This invention relates to novel pharmacologically active hydroxylated indanyl compounds, to a process for preparing such compounds and to pharmaceutical compositions containing those compounds.

SUMMARY OF THE INVENTION

In its process aspect, the present invention is a process for the preparation of indanyl compounds of the formula

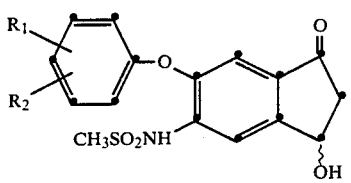

wherein $R_1$ and $R_2$, independently chosen, are hydrogen, fluorine, or chlorine, which comprises fermenting under aerobic conditions an indanyl derivative of the formula

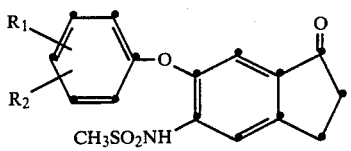

in the presence of *Aspergillus niger* or *Polyporus tulipiferus* in a medium containing assimilable sources of carbon and nitrogen.

In another aspect, the present invention is the compounds thereby produced and pharmaceutical compositions containing those compounds.

DETAILED DISCUSSION

The process of the invention is conducted under the conditions customarily employed in the microbiological hydroxylation of substrates with fungal cultures. First, the most favorable fermentation conditions are analytically determined, especially by means of thin-layer chromatography, such as, for example, selection of the most advantageous nutrient medium, the suitable substrate solvent or suspension agent, the substrate concentration, the technical conditions, such as temperature, aeration, pH value, and the optimum times for germination, substrate addition, and substrate contact on the enzyme of the microorganism.

It was found in this connection that it is advantageous to utilize concentrations of about 100 to 2,000 mg of substrate per liter of nutrient medium. The pH is preferably adjusted to a value in the range from 5 to 7. The cultivation temperature lies in the range from 20° to 40° C., preferably 25°–35° C. For aeration, 0.5–5 liters of air is preferably supplied per minute per liter of culture broth. The conversion of the substrate is suitable monitored by analyses of sample extracts.

The *Aspergillus niger* and *Polyporus tulipiferus* microorganisms utilized for the fermentation are readily available from conventional sources such as depositories, university collections, etc.

Preferred strains are *Aspergillus niger* ATCC 10577 and NRRL 3228, and *Polyporus tulipiferus* CBS 43148.

After fermentation has taken place, the products of fermentation are isolated by conventional means. Isolation can be accomplished, for example, by extracting the fermentation batches with a water-immiscible organic solvent, such as ethyl acetate, butyl acetate or methyl isobutyl ketone, concentrating the extracts, and purifying the resultant crude product optionally by chromatography and/or crystallization.

The compounds of this invention exhibit good antiphlogistic activity. They also exhibit activity as analgesics, antidysmenorrheics, antipyretics, thrombocyte-aggregation-inhibitors and diuretics. It is noteworthy that these compounds having little effect in inhibiting prostaglandin synthesis. A further advantage of these compounds is the large margin between therapeutic efficacy and undesirable side effects, particularly ulcerogenesis.

Consequently, the novel comounds of the present invention, in combination with the excipients usually employed in galenic pharmacy, are suitable for the treatment of a wide array of rheumatic type diseases, such as rheumatoid arthritis, osteo-arthritis and ankylosing spondylitis. They are also suitable for the treatment of bronchial asthma, hay fever, migraine and dysmenorrhea, and reduce the risk of thrombosis.

Certain of the indanyl compounds of the invention, surprisingly additionally exhibit pronounced antiulcerogenic activity.

Pharmaceutical dosage composition containing these compounds are produced in the usual way by blending the active compounds with suitable additives, excipients, and flavoring agents into the desired forms of administration, such as tablets, dragees, capsules, solutions, inhalants, etc. Especially suitable for oral administration are tablets, dragees, and capsules which contain, for example, 1–250 mg of active compound and 50 mg to 2 mg of a pharmacologically inert carrier, such as, for example, lactose, amylose, talc, gelatin, magnesium stearate, and similar materials, as well as the usual additives.

The starting compounds for the process of this invention are known or can be prepared in a manner known per se (U.S. Pat. No. 4,244,960 and 4,375,479).

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

EXAMPLE 1

A 2-liter Erlenmeyer flask filled with 500 ml of a sterile, aqueous nutrient solution containing

| | |
|---|---|
| 3.0% | glucose |
| 1.0% | corn steep liquor |
| 0.2% | sodium nitrate |
| 0.1% | potassium dihydrogen phosphate |
| 0.2% | dipotassium hydrogen phosphate |
| 0.05% | magnesium sulfate heptahydrate |
| 0.002% | iron (II) sulfate heptahydrate |
| 0.05% | potassium chloride | is inoculated with an agar slant of the strain *Aspergillus niger* ATCC 10577 or *Aspergillus niger* NRRL 3228 and shaken for 60 hours at 28° C.

The contents of the flask are then transferred under sterile conditions into a 20-liter preliminary fermentor charged with 15 liters of the same nutrient solution. With the addition of silicone SH as a defrother, germination is effected at 29° C. and a pressure of 0.7 bar (over atmospheric) with aeration (15 liters per minute) and agitation (220 rpm) for a period of 24 hours.

Thereafter, 0.9 liter of its contents is withdrawn from the preliminary fermentor under sterile conditions and used to inoculate a 20-liter main fermentor containing 14 liters of the nutrient medium described above. After an incubating phase of 12 hours under preliminary fermentor conditions, a sterile solution of 3.0 g of N-[1-oxo-6-phenoxyindan-5-yl]methanesulfonamide in 60 ml of dimethylformamide is added thereto, and fermentation is carried out under the above-indicated conditions for 48 hours.

The culture broth is then extracted twice with 10 liter portions of methyl isobutyl ketone, the extract concentrated under vacuum, and the residue chromatographed over a silica gel column by means of dichloromethane-acetone gradients. On recrystallization from acetone-diisopropyl ether, there is obtained 1.74 g of N-[1-oxo-3β-hydroxy-6-phenoxyindan-5-yl]-methanesulfonamide, mp 148°-150° C.

EXAMPLE 2

Using the conditions of Example 1 and using the microorganism *Polyporus tulipiferus* CBS 43148, 3.0 g of N-[1-oxo-6(2,4-difluorophenoxy)indan-5-yl]methanesulfonamide is hydroxylated for a period of 46 hours. After working up the reaction mixture and purifying the cruide product by column chromatography on silica gel, 0.96 g of N-[1-oxo-3β-hydroxy-6-(2,4-difluorophenoxy)indan-5-yl]methanesulfonamide is obtained in the form of a colorless oil which crystllizes after standing for several days in a refrigerator; mp 83°-86° C.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A compound of the formula

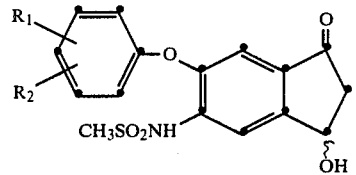

wherein $R_1$ and $R_2$, independently chosen, are hydrogen, fluorine or chlorine, with the proviso that $R_1$ and $R_2$ are not both H.

2. N-[1-oxo-3β-hydroxy-6-(2,4-difluorophenoxy)indan-5-yl]methanesulfonamide, a compound according to claim 1.

3. A method of achieving an antiphlogistic effect in a patient comprising administering a composition of claim 1.

4. A pharmaceutical composition comprising an antiphlogistically effective amount of a compound of claim 1 and a pharmaceutically acceptable carrier.

5. A pharmaceutical composition comprising an antiphlogistically effective amount of substantially pure, antiphlogistically administrable N-(1-oxo-3-hydroxy-6-phenoxyindan-5-yl)methane-sulfonamide.

6. A method of achieving an antiphlogistic effect in a patient comprising administering an effective amount of substantially pure, antiphlogistically administrable N-(1-oxo-3-hydroxy-6-phenoxyindan-5-yl)methanesulfonamide.

* * * * *